US007695953B2

(12) United States Patent
Gould et al.

(10) Patent No.: US 7,695,953 B2
(45) Date of Patent: Apr. 13, 2010

(54) APPARATUS FOR HIGH-SENSITIVITY BODY FLUID TESTING DEVICE

(75) Inventors: Martin Gould, Mullica Hill, NJ (US); Robert Smalley, Woodbury, NJ (US); Robert Bernstine, Chesapeake City, MD (US); Jackie Gale, Hants (GB); John Donovan, Logan Township, NJ (US)

(73) Assignee: American Bio Medica Corporation, Kinderhook, NY (US)

( * ) Notice: Subject to any disclaimer, the term of this patent is extended or adjusted under 35 U.S.C. 154(b) by 401 days.

(21) Appl. No.: 11/621,261

(22) Filed: Jan. 9, 2007

(65) Prior Publication Data

US 2008/0166820 A1 Jul. 10, 2008

(51) Int. Cl.
 *G01N 33/533* (2006.01)

(52) U.S. Cl. ............... 435/287.2; 435/7.1; 435/287.9; 436/514; 436/518; 436/165; 436/174; 422/58; 422/61; 422/102

(58) Field of Classification Search .......... 422/58, 422/61, 102; 436/165, 174, 514, 518; 435/7.1, 435/287.1

See application file for complete search history.

(56) References Cited

U.S. PATENT DOCUMENTS

| 5,234,813 | A | * | 8/1993 | McGeehan et al. ........... 435/7.9 |
| 5,630,986 | A | | 5/1997 | Charlton et al. |
| 5,726,013 | A | * | 3/1998 | Clark ........................... 435/5 |
| 5,830,154 | A | | 11/1998 | Goldstein et al. |
| 6,214,629 | B1 | | 4/2001 | Freitag et al. |
| 6,267,722 | B1 | | 7/2001 | Anderson et al. |
| 6,365,417 | B1 | * | 4/2002 | Fleming et al. ............. 436/514 |
| 6,464,939 | B1 | | 10/2002 | Bachand et al. |
| 6,468,474 | B2 | | 10/2002 | Bachand et al. |
| 6,489,172 | B1 | | 12/2002 | Bachand et al. |
| 6,524,530 | B1 | | 2/2003 | Igarashi et al. |
| 6,634,243 | B1 | | 10/2003 | Wickstead |
| 2005/0177072 | A1 | | 8/2005 | Kloepfer et al. |

FOREIGN PATENT DOCUMENTS

EP          520 408        12/1992

* cited by examiner

*Primary Examiner*—Bao-Thuy L Nguyen
(74) *Attorney, Agent, or Firm*—B. Aaron Schulman; Stites & Harbison PLLC

(57) ABSTRACT

An extraction method and apparatus is provided for obtaining quick, safe and highly sensitive testing of any of a variety of body fluids including saliva, blood, urine or other fluids for drugs of abuse or other analytes. The apparatus includes a latchable extraction wand for obtaining body fluid samples from a subject which is adapted to maximize the portion of the body fluid sample that will go into a graduated bottle containing a buffer solution, and a testing device wherein the sample will be received and into which test strips can be inserted to determine levels of drugs of abuse or other analyte in the sample. In one of the methods of the invention, energy is imparted to the sample and buffer solution, such as by shaking, and this facilitates the reduction of sample viscosity, such as by promoting the breakdown of mucins when the sample is saliva.

14 Claims, 12 Drawing Sheets

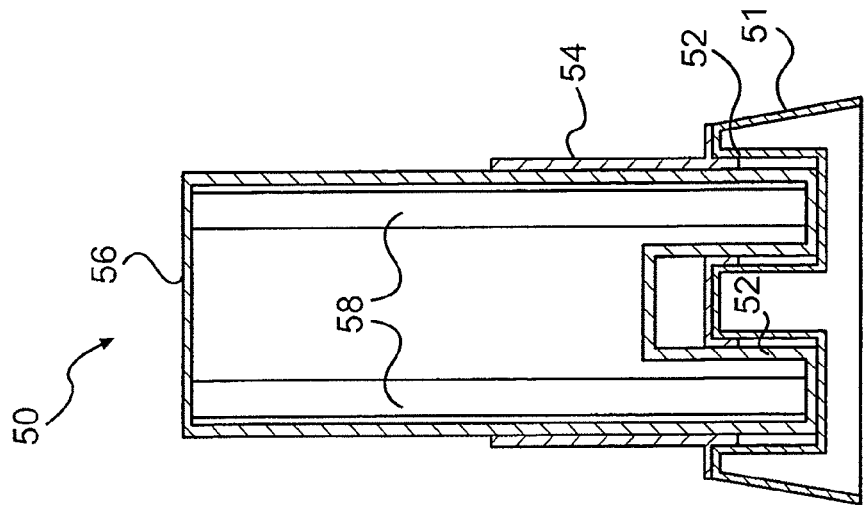
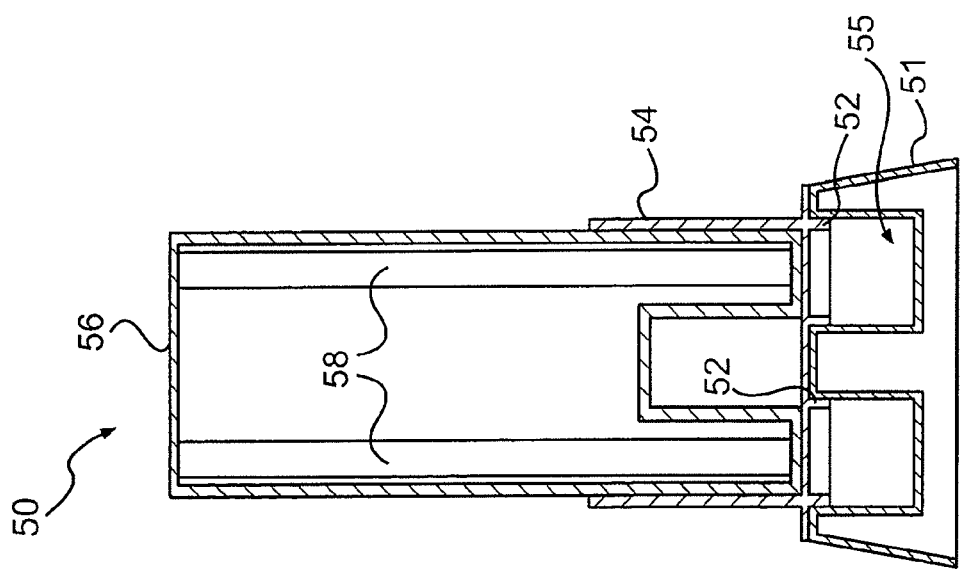

APPARATUS FOR HIGH-SENSITIVITY BODY FLUID TESTING DEVICE

FIELD OF THE INVENTION

The present invention relates generally to diagnostic testing of body fluids such as saliva, blood and other fluids for analytes including drugs of abuse and other compounds and materials, and more particularly to an extraction method and apparatus which maximizes the sensitivity of the testing device and which allows for the safe and convenient testing of even small quantities of a desired analyte from a body fluid sample.

BACKGROUND OF THE INVENTION

The increased availability and use of drugs of abuse along with the need for testing of other analytes, for example HIV or antibodies thereto, has caused employers, governmental agencies, sports groups, hospital emergency rooms and other organizations to utilize drug and analyte screening methods in a wide variety of situations such as in screening individuals for potential employment or purchasing insurance, or in order to maintain safety in the work place. In addition, in law enforcement, there is a constant need for providing improved on-the-spot testing for drugs of abuse or other analytes in a quick and simple manner since these tests will be far removed from the clinical setting. Screening tests for the detection of drugs of abuse and other analytes range in complexity from simple immunoassay tests to very complex analytical procedures.

Over the years the speed and specificity of immunoassays have made them one of the most accepted methods for screening for drugs of abuse in body fluids. Typical drug screening tests are performed for the purpose of quickly identifying on a qualitative basis, the presence of drugs in a body fluid which may be urine or saliva. A complete analysis of the sample may then be carried out in a laboratory only if the preliminary screening results are positive. More and more such drug screenings are taking place on site or at the work place, or during routine police stops or check points, and these are generally carried out by testing personnel who are generally not technically trained as would be a laboratory technician. It is thus important that the drug screening procedure is simple but yet reliable. Further, the test apparatus must be designed so as to enable the testing personnel to avoid all contact with the fluid specimen which is being tested.

While blood and urine samples have long been the primary fluids used for testing for disease as well as for evidence of substance abuse, there is increasing interest in testing regimens which can test a variety of body fluids including salivary specimens. Some advantages in a system that can test saliva in addition to bodily fluids such as blood and urine is that it is relatively easy to obtain a saliva sample and that a saliva sample obtained on the spot cannot be adulterated. Also, saliva testing is more suitable in testing of recent use since it does not maintain reactivity of the analyte after use for up to four to six weeks. Accordingly, testing of saliva gives a result in real time within a span of hours as compared to urine which gives a test result after-the-fact. In general, saliva and blood are useful to measure impairment, while urine tests generally are not suitable for this purpose.

However, the ability to collect and analyze saliva samples in addition to other bodily fluids using an immunoassay for diagnostic purposes is complicated by the relatively high viscosity of the fluid and the small volumes of salivary fluid secreted. In particular, saliva contains mucins which are a family of large, heavily glycosylated proteins which account for many of the properties of saliva. These mucins also act to disrupt or inhibit the lateral flow necessary to achieve a rapid and accurate test result and greatly restrict both the time it takes for a sample to travel through the immunoassay strip as well as the amount of the target compound in the sample which can travel up the strip and thus be determined by the immunoassay.

Because of the problems caused by mucins, certain testing systems had recommended long and elaborate procedures for removing mucins prior to testing the sample. These procedures include pre-treating a sample such as saliva with a diluent or other reagent which is capable of breaking down the interferants in a sample, e.g., mucins in saliva, so that these interferants do not restrict the capillary flow of the sample through the test strip, in order to try to achieve a rapid test of target compounds. However, these pre-treatment steps with specific reagents to dilute or denature interferants, modify analyte structure, or release analyte from binders, must generally be performed outside the confines of the test device, and this incurs additional steps and solutions which must be handled by the persons administering the test. For example, it is necessary to suitably collect the sample, have the sample expressed into a buffer solution, and then dispensed into a reaction well which generally contains a second reagent such as an identifying reagent, all before the testing solution including the sample is introduced onto an immunoassay test strip. All these steps necessitate the development of means and techniques for constructing self-contained devices which can test for saliva in addition to other body fluids in a manner that allows one to safely and efficiently control the test sample during pre-treatment and testing, but is still safe and simple to use and also able to obtain accurate results.

Previously, others have attempted to develop devices to test saliva, but none have provided a safe, quick and effective means for testing a variety of body fluids including saliva which can be used in a variety of settings including on-the-spot testing in addition to testing in the workplace setting by non-professional testing personnel. For example, U.S. Pat. No. 6,634,243 issued to Wickstead relates to a device which has an inadequate and ineffective provision for control of the test sample. Other art in this field includes U.S. Pat. Nos. 6,267,722 issued Anderson et al, 6,214,629 issued to Freitag et al., and 5,630,986 issued to Charlton et al. In addition, U.S. Pat. Nos. 6,464,939, 6,468,474 and 6,489,172, each issued to Bachand et al, disclose other saliva testing devices which also do not allow for quick and efficient break down of mucins so as to facilitate a highly sensitive test for a drug of abuse from a saliva sample. Finally, other devices are shown in U.S. Pat. No. 6,524,530 and in European Patent Application 520,408 A1, but once again these references do not disclose a flexible testing system which can suitably handle the problems associated with saliva testing and at the same time be able to readily test other bodily fluids for drugs of abuse and/or other analytes.

It thus remains a highly desirable object to develop methods and devices which allow for quick, safe and accurate testing of drugs of abuse or other analytes from a variety of body fluids including saliva, and which can be used conveniently and effectively in a wide variety of settings, including on-the-spot testing.

SUMMARY OF THE INVENTION

It is thus an object of the present invention to provide a safe and effective method and apparatus for performing a quick and accurate test for analytes such as drugs of abuse from a variety of body fluids including saliva in a quick and efficient manner.

It is another object of the present invention to provide such a body fluid testing device that allows the test sample to be treated and properly incubated prior to being introduced to the test strip.

It is a further object of the present invention to provide a body fluid testing device which is particularly adapted to receive a sample, extract the sample by treating it with a buffer, and ultimately introduce the sample to an identifying reagent which allows for qualitative, quantitative, or semi-quantitative identification of the drugs of abuse or other analytes in the sample.

It is an additional object of the present invention to provide such a body fluid test device that provides ready access to a reaction well for a test sample which is then contacted by a test strip.

The objects of the present invention are achieved and the disadvantages of the prior art are eliminated by the body fluid test device according to the present invention in which a device for testing a variety of body fluids including saliva is provided wherein an elongated wand containing an absorbent collector sponge is utilized to collect samples from the subject, and this wand is configured with a latchable internal cavity which allows the wand to be placed in a locked position applying compression to the sponge so as to maximize the extraction of the body fluid from the sponge located at the distal end of the wand.

In operation, once the sponge at the end of the wand is used to obtained a suitable body fluid sample from the subject, the wand is then placed into a suitable container or vial containing a buffer solution and then brought downward so that a latch mechanism is engaged so that the wand can provide maximum compression to the sponge and ensure that the extraction of the body fluid from the sponge is maximized. The buffer solution will be utilized to prepare the sample for immunological testing, such as by breaking down mucins when the sample tested is saliva. In general, the use of a buffer solution will allow for a more sensitive test for the drug or other analyte of interest. This buffer solution may be stored in a graduated bottle which allows for the quantification or semi-quantification of the testing procedure. It is preferred that the buffer be formulated to solubilize the analytes of interest, thereby making them available to react with the labeled antibodies in an immunoassay.

Once the extraction wand has been primed so as to release the maximum amount of body fluid into the buffer solution, one may impart energy to the buffer solution and test sample in order to further assist in preparing the sample for the immunological testing, such as by breaking down mucins when the sample is saliva, or otherwise reducing the viscosity of the body fluid sample by removing or denaturing interferants which will improve its ability to be tested in a lateral flow or other immunoassay. By imparting energy is meant the application of energy to aid in the reduction of viscosity, such as by agitation or shaking, chemical reaction, or other means of providing energy to assist in the breakdown of the sample.

In the preferred process of the invention, following a suitable time for incubation in the buffer solution, wherein the buffer container or vial may be shaken so as to impart energy into the solution and assist in the breakdown of the interferants in the sample, the buffer solution containing the sample is next transmitted via a pipette or dropper into reaction wells which contain a suitable conjugating identifying reagent, or marker, tag or label. Such identifying reagents are well known in the field of analyte testing and may include materials such as antibodies conjugated to gold colloid particles, or other means of labeling such as enzymes and substrates, fluorescent compounds, or other metal colloids, which will act in order to form a suitable label for the target drugs of abuse. At this point, the combination of buffer, sample and identifying reagent may once again be shaken or otherwise agitated or mixed to impart energy and afford a further reduction of viscosity, such as by enhancing the breakdown of mucins when the sample is a saliva sample, so as to enhance the immunological reaction and improve the efficacy of the immunoassay and thus provide a more accurate and sensitive reading of the target drugs or analytes in the sample. Finally, after a suitable incubation period, an immunoassay test strip is allowed to enter the reaction wells containing the sample and buffer solution, or alternatively the buffer solution containing the sample is otherwise allowed to be introduced to the test strip, such as by the removal of a barrier or membrane between the reaction wells and the test strip. In either case, the test strip will operate via lateral flow so as to identify the presence and/or level of a target drug or analyte in the sample at a high level of sensitivity because of the removal of interfering particles in the sample solution.

In the preferred embodiments of the invention, the testing system includes a test device for housing the reaction wells and immunoassay test strip. This may include a device which has a base housing upon which is mounted an upper housing. In one such embodiment, the base housing is a means for defining at least one reaction well to receive fluid specimens to be tested. In the case wherein multiple test strips are desired, such as to detect the presence of more than one drug of abuse or analyte at the same time, two or more reaction wells may be provided in the testing device. In one such embodiment, the upper housing may comprise a hollow tubular structure and is mounted in such a position so that its interior communicates with the reaction wells. A test strip or strips may be movably supported in the upper housing such that the test strip can be placed into a reaction well to contact a fluid test specimen therein. Alternatively, the test strip may be separated from the reaction well using a suitable membrane or other barrier which is removed or which dissolves after a given amount of time so as to allow the sample solution to be introduced to the immunoassay test strip. In still another embodiment of the invention, the reaction wells may be sealable to allow the proper mixing of the sample, buffer and identifying reagent for a suitable time without spillage. In addition, the sealing of the reaction wells allows the sample solution to be shaken so as to impart energy and further breakdown the mucins in the saliva sample and further increase the sensitivity of the testing procedure.

Other embodiments include a system wherein the reaction well means may be capped so that the solution of sample and buffer may mix with the label such as colloidal gold particles and an appropriate antibody or antigen without any danger of the solution spilling out of the reaction well, and the capping of the reaction wells also permits additional shaking as desired to even further impart energy to the solution and afford even greater breakdown of mucins and increase the sensitivity of the testing without spilling the solution. In such a system, there is generally provided a barrier or membrane which keeps the sample, buffer and label apart from the test strip until sufficient time has been provided for the incubation of the sample solution and label, and this barrier or membrane may be removed when it is desired to have the sample solution contact the test strip and allow for the lateral flow immunoassay to take place.

In other embodiments, the testing device may include an upper housing wherein there is a movably mounted support member upon which one or more test strips may be mounted. A manually operated trigger is attached to the strip support member and protrudes outwardly of the upper housing. The trigger can be pushed downwardly to place a test strip into a reaction well when desired to run the test. The upper housing preferably also has an opening through which the result portion of the test strip is exposed such that a test result can be viewed through the opening, as described further below.

In the general process for collecting and testing a bodily fluid such as saliva in accordance with the invention, the sponge end of a collector wand is used to collect and absorb the bodily fluid, and when the fluid is saliva, the wand if inserted into the mouth of the person to be tested. The inside of the mouth and tongue are actively swabbed until the sponge becomes fully saturated. The collector is removed from the mouth and the oral fluid is extracted from the sponge end into a suitable container or vial which preferably contains a buffer agent or other reagent which can begin the process of breaking down mucins in the saliva. This container or vial is preferably sealed such as with a removable cap so that one may also impart energy to the container or vial such as by shaking in order to promote the mixing of the sample and the buffer. The resulting mixture is then dispensed into a reaction well of the test device into which may have been previously placed a second reagent which is preferably a binder or other identifying reagent such as a colloidal gold-antibody complex or an antigen. The second reagent may be in the form of a dry dot or a pellet, or even other forms such as liquid, powder, paper, etc., as would be needed for particular testing procedures. After a period of incubation of the test mixture with the second reagent, a test strip is moved into the reaction well, or the test strip is otherwise allowed to contact the sample solution such as by the removal of a barrier between the reaction well and the test strip, so that the sample receiving end of the test strip contacts the fluid specimen within the reaction well. Following the movement of the sample via capillary action in the test strip, the test result is then subsequently viewed on the test result portion of the test strip to determine if the target drug or analyte is present.

Other features and advantages of the present invention will be described in, or will be obvious from, the detailed description provided hereinbelow

BRIEF DESCRIPTION OF THE DRAWINGS

Other objects and advantages of the present invention will be apparent upon reference to the accompanying descriptions when taken in conjunction with the following drawings, which are exemplary, wherein:

FIG. 10b is a side, partially cut-away view of the alternate embodiment as depicted in FIG. 10a.

FIGS. 11a-e show various views of yet another alternate embodiment of the testing device of the present invention.

DETAILED DESCRIPTION OF THE INVENTION

Proceeding next to the drawings wherein like reference symbols indicate the same parts throughout the various views, the present invention including exemplary embodiments and modifications thereof, will be described in detail.

In accordance with the present invention, a body fluid testing device is provided wherein an elongated wand containing a collector sponge at its distal end is utilized to collect fluid samples from the subject, and this wand is configured with handle means capable of compressing the sponge and a latchable internal cavity which allows the wand to be locked into a compressed position to allow the maximization of the extraction of the body fluid from the sponge when the handle is brought down over the sponge and latched into the locked position. The present device is capable of testing a variety of collectable body fluids, including fluids such as saliva, blood, urine, cerebrospinal fluid, nasal fluid, buccal cavity scrape/ swab, tears, sweat, vaginal secretions, ear wax, and other bodily fluids. In accordance with the invention, the present system can be used in immunoassay tests for a variety of analytes, i.e., constituents or materials which can be detected or measured from the body fluid of a subject, and such analytes include drugs of abuse, chemical compounds such as glucose, insulin, proteins, bilirubin, urobilinogen, ketones, and other biological materials such as viral particles, e.g., HIV and leukocytes. With regard to drugs of abuse, the present invention can be used with any of those drugs commonly tested, including amphetamines, benzodiazepines, cocaine, methadone, methamphetamines, opiates, phencyclidine (PCP) and THC (in either its parent form of metabolite form).

Figure 1:
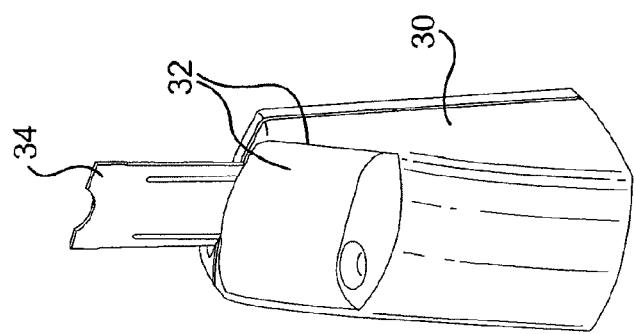
FIG. 1 is an overview of the testing system of the present invention including extraction collector wand prior to obtaining the test sample, a buffer vial for receiving the test sample, a pipette or dropper which can transfer the sample mixture into reaction wells, and a testing device containing the reaction wells and test strips for conducting the immunoassays to allow the qualitative or quantitative testing of drugs of abuse.
Figure 1:
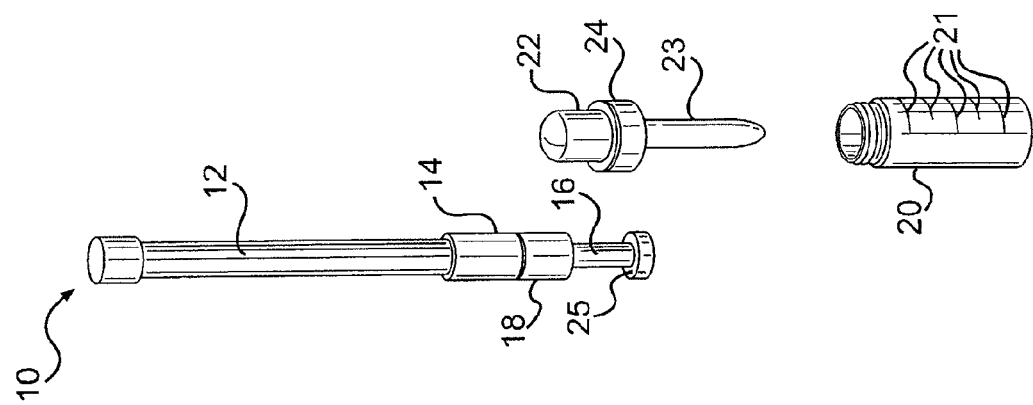

As will be described further below, the extraction wand 10 of the present invention is shown in the drawing of FIG. 1 which generally shows the parts of the extraction system of the present invention. This wand generally comprises a handle 12 having a hollow internal cavity having at least one latching means internally positioned for retaining a stem 16 constructed to fit slidably into the cavity so that the handle can slide downward over the stem and ultimately cause the sponge 18 to express the body fluid sample obtained from a patient. The handle will preferably have a generally cylindrical shape and will be configured so that the distal end 14 of the handle 12 will be able to apply compression to a sponge 18 positioned on the stem which will be used in the collection of a body fluid sample from the individual to be tested. Both the handle and stem may be made of a suitable sturdy sterilizable material such as hard plastic.

Figure 4B:
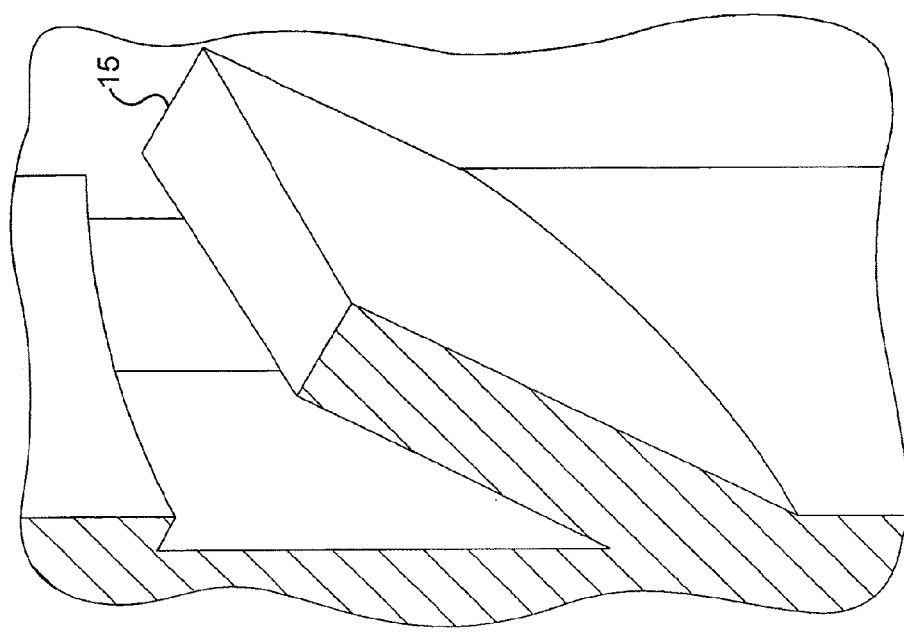
FIG. 4b is a perspective, close-up view of the latching means on the inside portion of the collector handle of the present invention
Figure 4A:
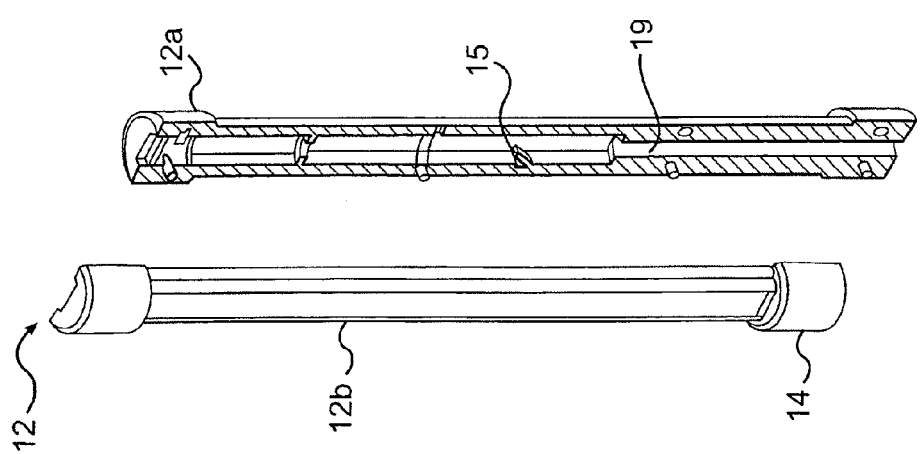
FIG. 4a is a perspective view of the two pieces forming the handle of the collector wand of the present invention showing the internal structure and latching means.

As shown best in FIGS. 4a and 4b, the handle may be constructed in two pieces 12a and 12b which can be placed together to form the handle. In the preferred embodiment, each half of the handle may have an internal channel which forms the internal cavity of the handle when the two halves are mated. The halves may be joined in any suitable manner, such as by matching pegs and holes, as shown in FIG. 4a. In addition, the handle features a latching means such as latch 15 which will allow the handle to be locked in position when compression of the sponge is desired to express the body fluid sample. In the preferred embodiment, the handle is generally cylindrical in shape, and at the distal end 14 is a portion that will be configured to apply compression to the sponge. In general, the end 14 will have a larger circumference than the central portion of the handle and will be roughly the same size as the sponge being compressed.

Figure 5B:
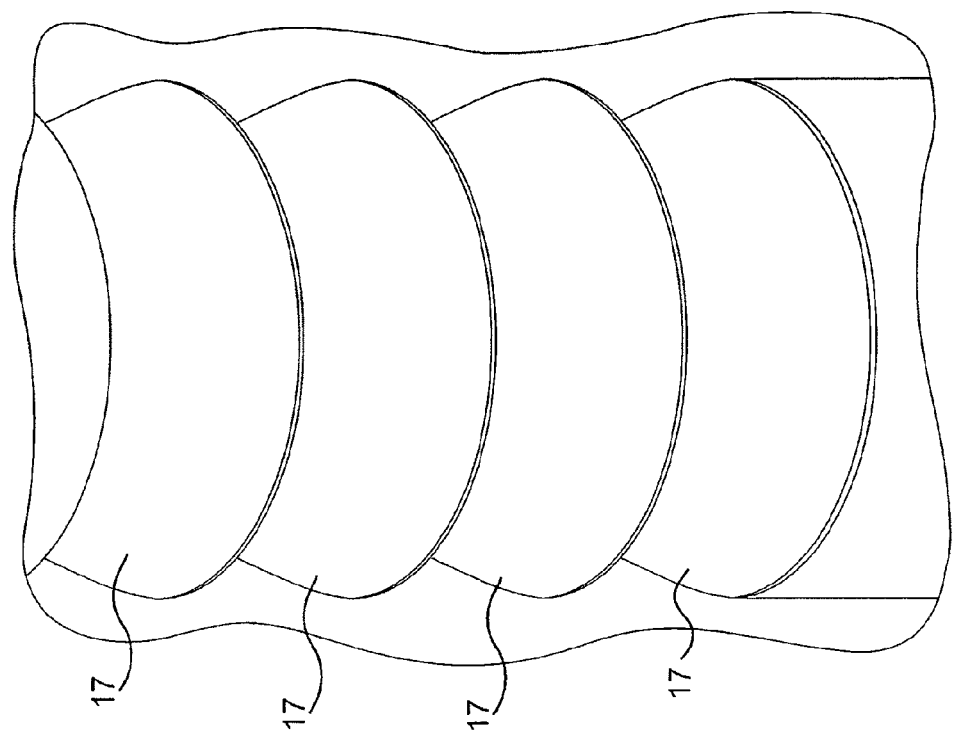
FIG. 5b is a perspective, close-up view of the protrusions on the stem which allow for the latching of the collector wand when desired to express the body fluid collected in the wand sponge.
Figure 5A:
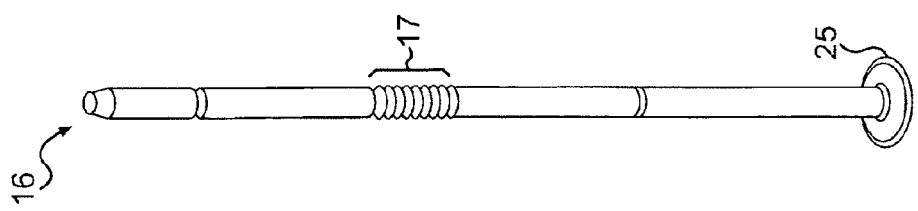
FIG. 5a is a perspective view of the stem which fits into the handle of the collector wand of the present invention.
Figure 6:
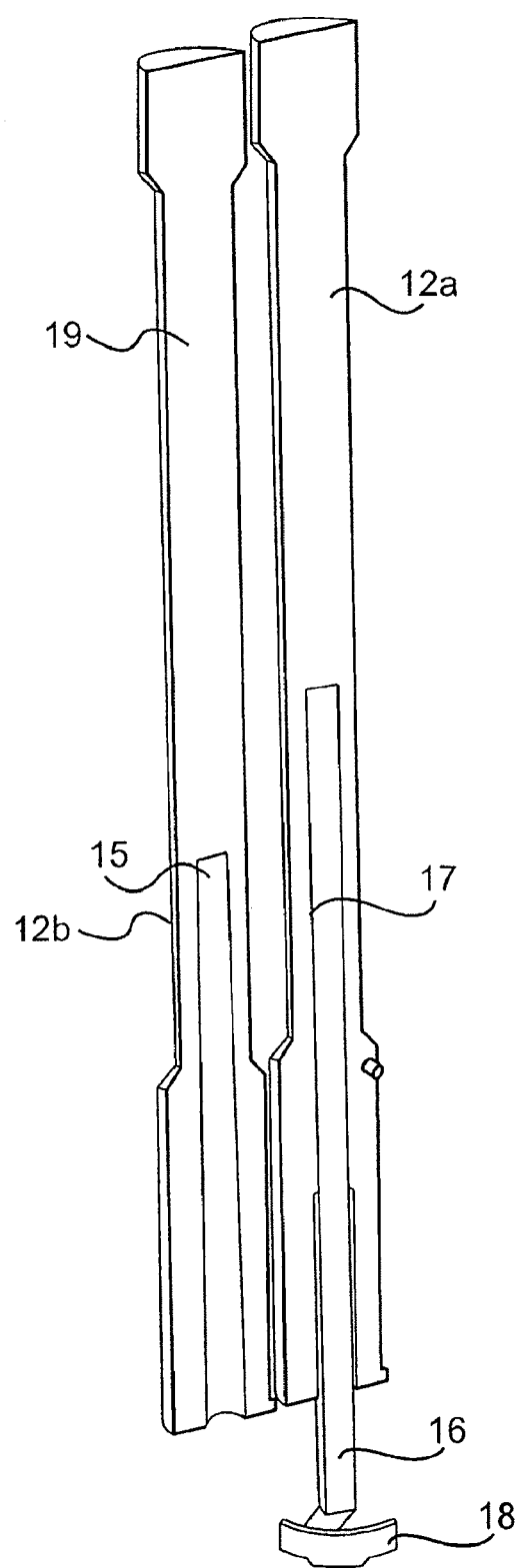
FIG. 6 is a front view of the two halves of the collector handle in open position which shows the internal latching means the internal positioning of the stem and sponge.

As shown best in FIGS. 5a and 5b, the stem 16 in the preferred embodiment is generally cylindrical and is sized to fit slidably into the internal cavity 19 of the handle. The stem may have a tapered end which will be the end that fits inside the handle as well as a flange or other flat disk 25 at its distal end which will remain outside of the handle and which will provide a supporting surface so that the sponge may be compressed when the handle is brought down on top of the sponge. In addition to being designed to fit slidably into the internal cavity 19 of the handle 12 and will have an exterior surface including at least one protrusion 17 at a suitable location away from the sponge end which can be retained by the latching means of the handle after the handle is brought down upon the sponge 18 so as to express the body fluid which has been collected in the first step of the testing procedure, as will be explained further below. The protrusion 17 will be constructed so as to be compatible with latching means 15 on the handle so that after the handle is brought down over the stem so that compression is applied to the sponge, the latch will lock on the protrusion in the stem so that the compressive force on the sponge will be maintained automatically so as to maximize the expression of the sample into the buffer vial as described below. In addition, the stem may contain a plurality of protrusions, to provide additional latching positions if so desired. As shown in FIG. 6, wherein the two pieces of the handle 12a and 12b, are shown in an open form before the handle is constructed by mating pieces 12a and 12b, the stem 16 has at least one protrusion 17 and fits slidably inside the internal cavity of the handle 12 which may be brought downward until the latching means 15 catches the protrusion 17 so as latch the handle in place to maximize compression of the sponge.

At the bottom end of stem 16, at the portion where the stem will be outside of the handle, there will be located a suitable sponge 18 capable of absorbing body fluids from the subject being tested. In the preferred embodiment, the sponge will be in the form of a compact disk which will be positioned on the distal end of the stem so that it is exposed and may be utilized to collect a sample from an individual who is being tested for the presence of drugs of abuse or other analytes. The sponge is preferably an untreated medical grade absorbent fiber sponge which will expand during the collection process, and if desired, more than one sponge may be used with the wand of the device.

As described herein, the present system includes means for buffering the body fluid sample before being introduced into the testing device, and in the preferred embodiment, this buffering means includes a buffer solution which is retained in a buffer vial designed to receive the expressed sample from the sponge of the collector wand after the handle is brought downward and the bodily fluid is expressed from the sponge. This buffer vial or container 20 is depicted in FIG. 1, and this vial may include gradations 21 so as to indicate the total volume of solution and to allow the testing of the present invention to be performed quantitatively or semi-quantitatively (i.e., those testing procedures which involve some aspects of quantitative testing and some which involve qualitative testing) in addition to qualitatively. The ability to use the graduated vial (and dropper or pipette as described below) for such quantitative or semi-quantitative testing so as to quantify when so desired the concentration of an analyte being detected by the testing device will be well understood by one skilled in the art. For example, the present invention will thus allow quantification in terms of weight and volume, i.e., measurements in terms of weight/weight or volume/volume will be made possible.

The extraction system of the present invention thus includes means such as vial 20 which is designed to receive the sample from the collection sponge and which preferably includes a buffer material which is designed to improve the sensitivity of the testing procedure such as by removing interfering particles from the sample solution and/or reducing the viscosity of the solution. As indicated above, the buffer solution is preferably one that is formulated to solubilize the analytes of interest, thereby making them available to react with the labeled antibodies in an immunoassay. In addition, the buffer is designed to remove or denature interferants so as to improve the ability of the sample material to be detected in a lateral flow immunoassay, and in the example when the body fluid being tested is saliva, the buffer solution can promote the breakdown of mucins in the saliva sample and enhance the sensitivity of the immunoassay based on this saliva sample. In general, the buffer solution will thus include those reagents which are capable of breaking down the interferants in a sample, e.g., mucins in saliva, so that these interferants do not restrict the capillary flow of the sample through the test strip, in order to have a rapid test of target compounds in a more accurate manner than heretofore possible. The buffer will thus be utilized in pre-treatment steps as appropriate for the body fluid being tested and will generally include specific reagents which can solubilize the analyte, dilute or denature interferants, modify analyte structure, and/or release analyte from binders Accordingly, the extraction buffer will generally be any suitable solution which serves to break down or remove interferants so as to reduce the viscosity of the oral fluid specimen, e.g., saliva, and ensure efficient capillary flow on the test strips, and such buffers are readily known in the art.

As indicated above, in order to carry out a testing procedure in accordance with the present invention, the collector wand 10 is swabbed in the subject at the appropriate location for the desired body fluid, e.g., the interior of the mouth or nose of a potential testing subject, so that the sponge 18 at the distal end of the wand will absorb the body fluid from the subject. As would be recognized by one skilled in this area, the collection of the body fluid will be conducted in a suitable manner appropriate to the particular body fluid which is the subject of the test. For example, if the fluid to be tested is saliva, tears, nasal fluid, ear wax or sweat, the sponge may simply be swabbed on the appropriate area of the subject. However, when the fluid to be tested is blood or cerebrospinal fluid, it may generally be necessary to remove such fluids or otherwise make the fluid available to the sponge for testing. For blood, this can be accomplished by venipuncture, and for cerebrospinal fluid, this might be accomplished by a lumbar puncture. Accordingly, the testing procedure may vary depending on the nature of the bodily fluid desired to be tested.

Figure 2:
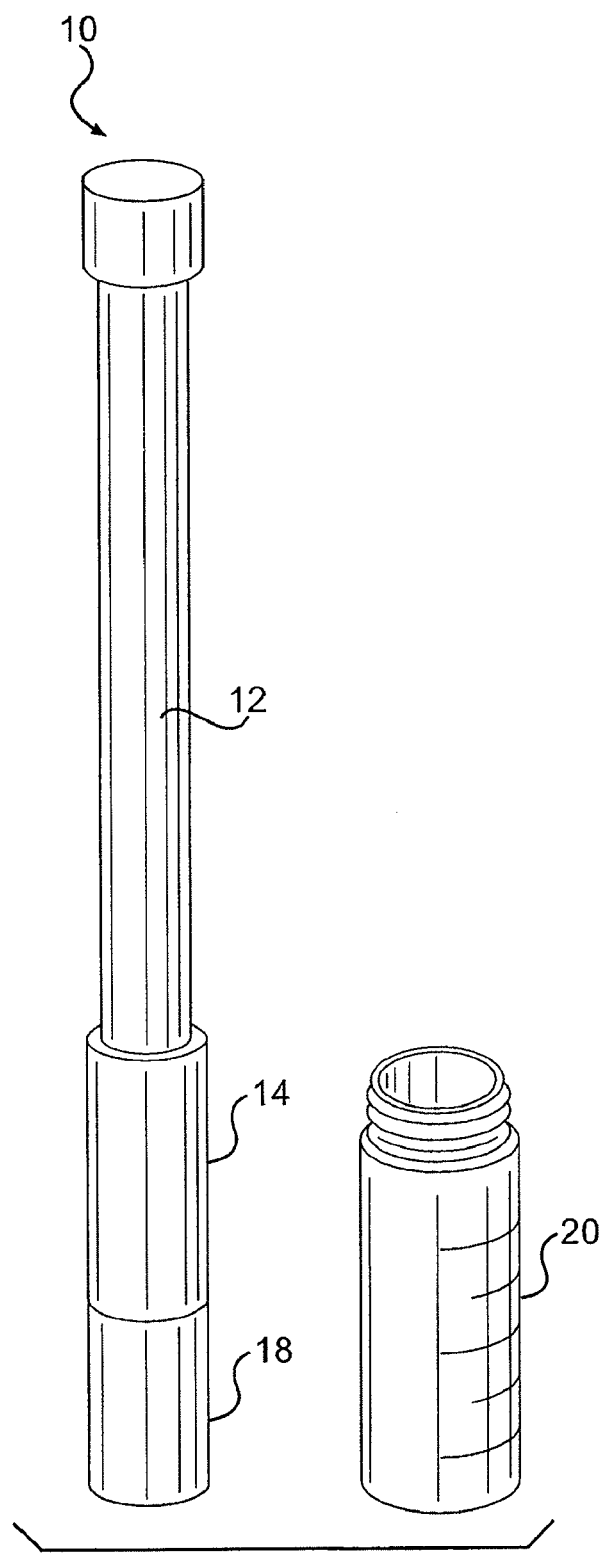
FIG. 2 is a front view of the collector wand and buffer vial following collection of the samples wherein the sponge at the distal end of the wand has expanded due to absorption of the sample body fluid.

In an exemplary process, the collector wand of the invention may be used to test a saliva sample, and this process will be described in more detail below, although one skilled in the art would recognize that the steps used in the collection process would vary as needed for other body fluids. In the preferred saliva collection process, the sponge of the collection wand is placed between the cheek and gum of the donor subject for at least one minute, during which time the subject is instructed to avoid any chewing or sucking action. During this time period, the sponge should expand which reflects the absorption of a suitable saliva sample, and in any event the procedure should continue until the sponge at the distal end of the stem is fully expanded, indicating that a suitable amount of saliva has been absorbed from the subject. This configuration is shown in FIG. 2 wherein the sponge 18 following collection of the sample of saliva from the subject has expanded and is ready for expression into buffer vial 20.

Figure 3:
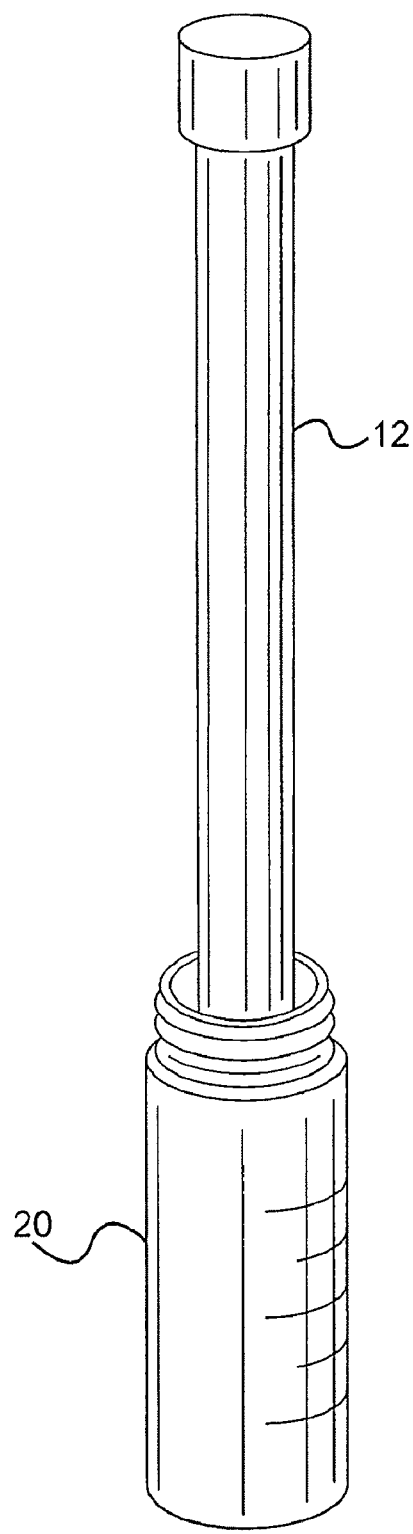
FIG. 3 is a front view of the collector wand inserted into the buffer vial so that the sample may be expressed from the sponge and mixed with the buffer solution in the vial.

Accordingly, at this point the collector wand 10 with its expanded sponge 18 which has been removed from the subject, is placed into the buffer vial 20 so that the sample may be fully expressed from the sponge and enter into the buffer solution contained in the buffer vial, and the placement of the sponge or distal end of wand 10 into buffer vial 20 is shown in FIG. 3. At this point, buffer solution from the vial 20 will initially be absorbed into the sponge 18, and as indicated above, the sample and buffer may be expressed from the collector wand by bringing the handle down towards the sponge so that the distal end of the handle compresses the sponge, and the handle will be brought into locking position when the latching means in the internal cavity of the handle is brought into contact with the outermost protrusion in the stem. This will lock the handle in position such that the compression of the handle over the sponge is maintained and the expression of the saliva sample into the buffer solution is maximized. Prior to bringing the handle into locked position, it may be preferable to ensure that the collector sponge is fully immersed in the buffer solution inside the buffer vial and that the collector wand be rotated to assist in the expression of the sample from the sponge to the buffer solution. In addition, once the saliva sample is fully expressed into the buffer vial, the buffer vial is preferably sealed, and preferably energy is imparted into the buffer and sample which will ensure thorough mixing of the sample in the buffer solution.

In this regard, although the buffer vial 20 may be sealed by any suitable means, it is preferred that a dropper or pipette 22 be utilized which will have a cap 24 that can seal the buffer vial 20. The dropper may suitably be threaded so that it can be resealed on top of the buffer vial by simple turning, and the dropper may also contain a fill line 23 so that a quantitative amount of the sample and buffer may be removed from the vial and used for testing in accordance with the invention. Once the saliva sample has been expressed in the buffer vial as indicated above, and once the buffer vial is sealed by means of dropper cap 24 or other capping means, the sealed buffer vial may be shaken so as to impart energy and promote the breakdown of the mucins of the saliva sample, which will ultimately enhance the sensitivity of lateral flow immunoassay tests conducted with regard to the drugs of abuse in the sample.

Accordingly, as indicated above, in the preferred operation of the present invention, the sponge at the end of the wand is used to obtained a suitable bodily fluid sample from the subject, and the sponge is place inside a buffer vial containing a buffer solution which will assist in the removal or reduction of interferants in the sample, e.g., mucins when the sample is saliva. Next, the wand is contracted until the latched position is reached by movement of the handle downward onto the stem so that a locked position is maintained so as to further express the bodily fluid from the sample into the buffer vial. As also indicated above, the buffer solution and sample may be mixed in order to further assist in the denaturation or removal of the interferants in the sample. This operation will allow for the body fluid used in the assay to be tested to a high sensitivity using an immunoassay test strip, as will be detailed below.

In the preferred testing process of the invention, following the expression of the sample in the buffer solution and the shaking of the sealed buffer container if necessary to assist in the breakdown of mucins, the buffer solution containing the sample may be transmitted via the dropper or pipette to reaction wells in a testing device wherein a suitable identifying reagent such as colloidal gold-labeled antibodies will be used in order to form a suitable label for the target drugs of abuse. In the preferred process, the testing device will be one which contains at least one, and preferably two, reaction wells containing a suitable identifying reagent, and will be one in which an immunoassay test strip is maintained outside of the reaction wells until such time as a suitable incubation period has elapsed which ensures that the identifying reagent will be sufficiently mixed with the buffer solution containing the sample body fluid expressed from the subject. One suitable testing device is known as the Oralstat® testing device available from American Bio Medica Corporation, Kinderhook, N.Y., but other suitable testing devices which can introduce a test strip into the incubated solution may also be used, such as described below. A testing device suitable for use with the present invention is also described in U.S. Pat. No. 7,090,803, said patent incorporated herein by reference.

Figure 7:
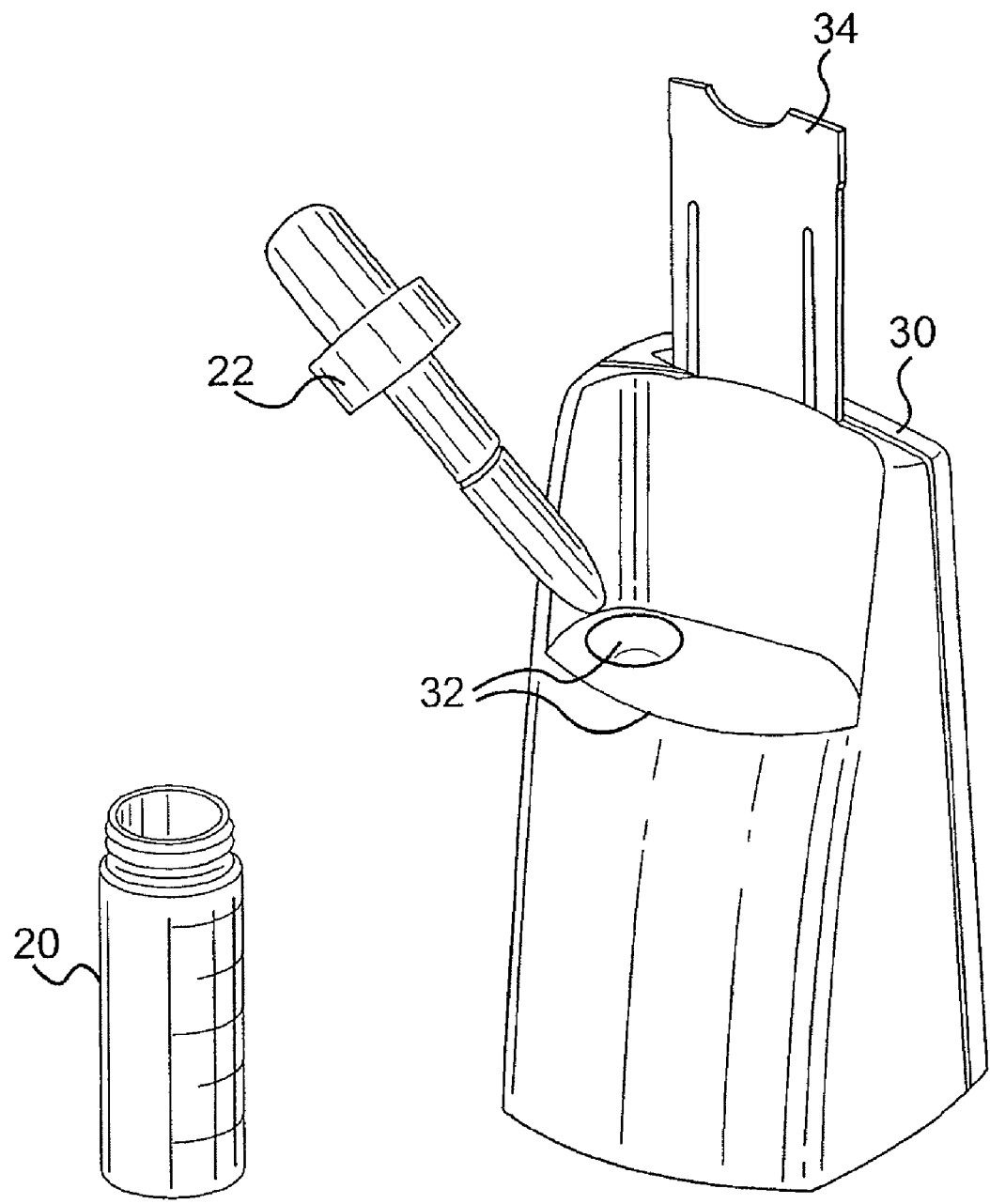
FIG. 7 is a schematic view of the injection of the sample solution into the reaction wells using the testing device in accordance with the present invention.
Figure 8:
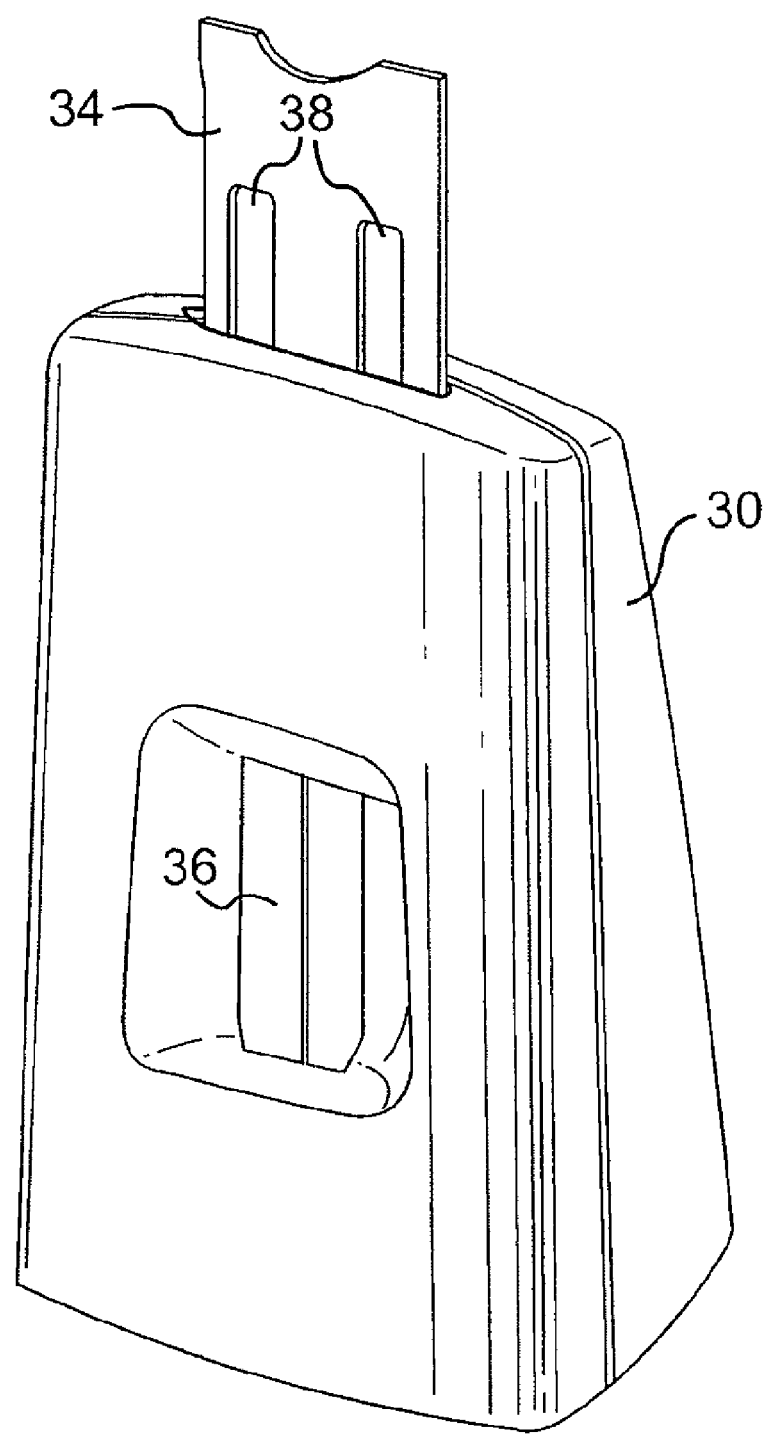
FIG. 8 is a rear view of an exemplary testing device in accordance with the present invention.

In accordance with the present invention, a suitable testing device 30 for use with the collector wand and buffer vial of the present invention, is shown in FIGS. 1, 7 and 8. The testing device 30 is preferably designed so that immunoassay test strips may be held outside the reaction well until it is time to conduct the immunoassay test, such as using means for holding 34 as shown in FIGS. 1, 7 and 8, and this holding means if preferably slidable so that the strips may be brought down into communication with the reaction wells after a suitable incubation time has elapsed. The device 30 also preferably contains an opening 36 at a location at the side of the device wherein the immunoassay test strips are housed so that the test results can be observed visually.

The testing device 30 contains one or more reaction wells 32 which may be used to retain a suitable identifying reagent such as a gold particle attached to a suitable antibody or antigen which can be used to target a particular drug of abuse or other analyte or material as described above. In one of the preferred embodiments of the invention wherein the analyte is a drug such as a drug of abuse, the drugs targeted by the test procedure can be any suitable drug or other compound of interest which may be detectable in a body fluid, and such drugs include amphetamines, benzodiazepines, cocaine, methadone, methamphetamines, opiates, phencyclidine (PCP) and THC (in either its parent form of metabolite form). The reaction wells or chambers thus will contain the desired identifying reagent, such as a gold-labeled antibody specific to the targeted drug or drugs of abuse, preferably in dried form or in other suitable forms as described above. This may take the form of a dry dot placed at the bottom of the reaction well. In the preferred process, when it is time to test the sample expressed in the buffer solution, the buffer solution may be introduced into the reaction wells 32 by use of the dropper 22 which has collected the solution from buffer vial 20. It is preferable that the dropper extract a predetermined amount of buffer solution from the vial, particularly when quantitative testing is desired, and this may be done by squeezing the dropper bulb so as to aspirate the sample to the fill line 23 on the dropper. The measured amount of sample may then be dispensed into the reaction well of the testing device.

In the preferred embodiment, once the buffer solution containing the sample is placed into the reaction wells containing the labeled antibodies, a suitable time period is allowed to elapsed before the test strips are introduced into the reaction wells. In general, the incubation time is necessary to allow the identifying reagent, such as gold-labelled antibodies, sufficient time to scavenge and bind the drug or analyte molecules in the fluid specimen, thus ensuring adequate sensitivity for the test.

In addition, in order to further promote the breakdown of mucins in the sample and give the test even greater sensitivity, it again may be desirable to impart further energy to the sample in the reaction well such as by shaking or agitation which can be done using the test device 30 by gently moving the device from side to side while on a flat surface. It is also possible to cap the reaction wells which would allow slightly more vigorous shaking to take place as needed. During the incubation period, the labeled antibodies will form bonds with the target drugs in the sample so that when the solution is introduced onto an immunoassay test strip, the presence or absence of the drug or other analyte at a particular location on the test strip will be indicated.

In the last step to conduct the immunoassays in accordance with the invention, following a suitable incubation period, one or more immunoassay test strips 38 are allowed to enter the reaction wells containing the body fluid sample, buffer, and identifying reagent, or are otherwise allowed to be introduced to the test strip, such as by the removal of a barrier or membrane between the reaction wells and the test strip. These test strips are well known in the art and are described, e.g., in U.S. Pat. App. Pub. 2001/0012637, said application incorporated herein by reference. In general, these test strips may be of the type made by companies such as Inverness Medical of Switzerland, Pharmatech of San Diego, Calif. and Arista Biological of Bethlehem, Pa. Such test strips are characterized as immunoassay strips and employ an identifying reagent based on colloidal gold chemistry. These test strips are configured so as to conduct a lateral flow immunoassay when one end is brought into contact with the test solution, and the results of the test are read in a test area preferably coinciding with a visual opening in the test device. As indicated above, these test strips can indicate the presence or absence of drugs of abuse including amphetamines, benzodiazepines, cocaine, methadone, methamphetamines, opiates, phencyclidine, PCP and THC, or other analytes when so desired.

In the testing device 30 as depicted in the drawing figures, the testing process is completed by allowing the test strip holder 34 to be lowered so that the lower end of the test strips in the older 34 can be placed in communication with the bottom of the reaction wells 32. This may be done by placing arms on the sides of the holding device which are pushed inward when it is desired to lower the test strips into the reaction wells. In either case, the test strip will operate via lateral flow so as to identify the presence and/or level of a target drug or analyte in the body fluid sample at a high rate of sensitivity due to the removal or breakdown of interferants by the buffer solution.

Figure 9:
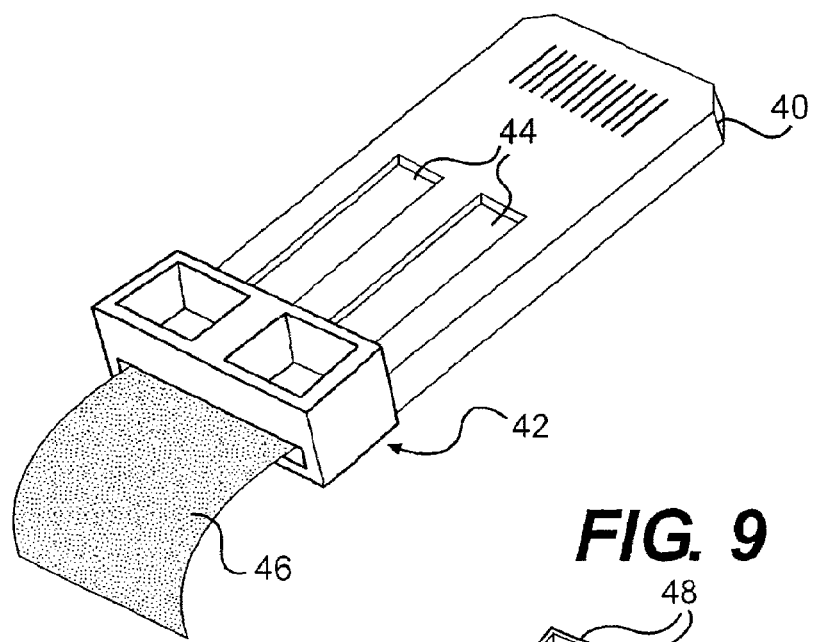
FIG. 9 is a perspective view of an alternate embodiment of the testing device of the present invention.

Alternatively, the test strip may be separated from the reaction well using a suitable membrane or other barrier which is removed or which dissolves after a given amount of time so as to allow the sample solution to be introduced to the immunoassay test strip. Alternative test devices incorporating such a barrier are shown in FIGS. 9 and 10. In FIG. 9, this alternative test device 40 is shown with modified reaction wells 42 which are placed over a housing which includes test strips 44. In this configuration, the buffer solution containing the body fluid sample which is obtained as outlined above is poured directly into the reaction wells which contain the gold-labelled antibody or other suitable binder or identifying reagent. The buffer and sample are allowed suitable time to mix with the antibody, and after a suitable incubation period has elapsed, and removable barrier strip 46 is provided between the bottom of the reaction well and the immunoassay test strip which is removed so that the labeled sample solution can now contact the immunoassay test strip and begin the lateral flow immunoassay test.

Figure 10A:
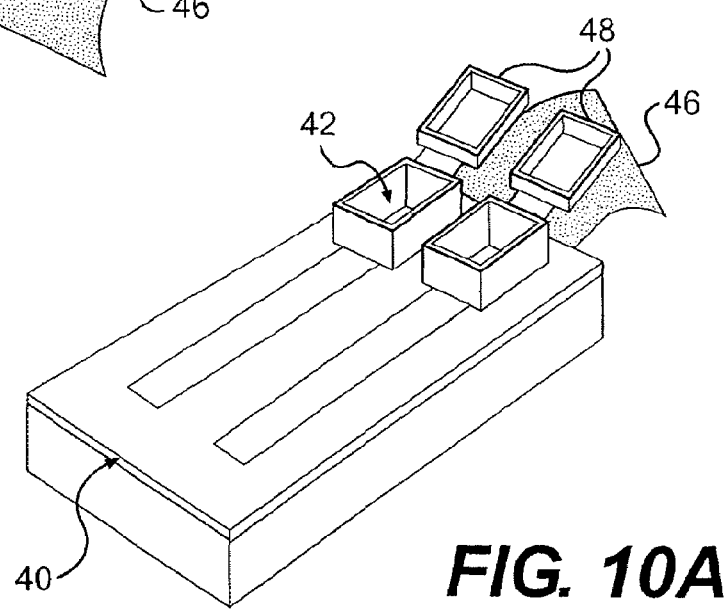
FIG. 10a is a perspective view of an alternate embodiment of the testing device of the present invention.
Figure 10B:
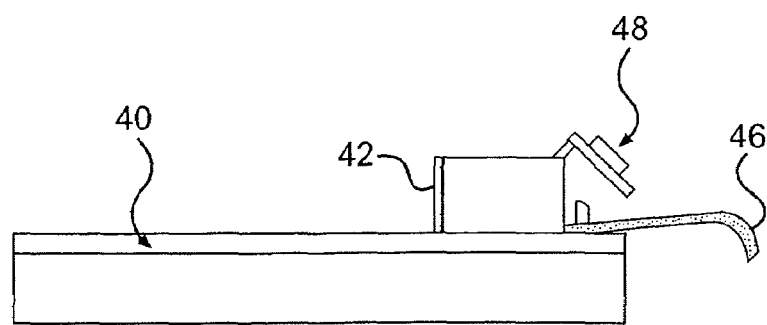

In a further alternative embodiment, such as shown in FIGS. 10a and 10b, the reaction wells 42 may be made sealable by providing caps 48 which fit tightly over the reaction wells and seal them after the solution has been placed in the wells. In this embodiment, the sealing of the reaction wells allows for the sample and buffer solution to be further mixed with the colloidal gold by shaking or otherwise imparting energy to the wells, and this will once again facilitate mixing of the solution and the breaking down of the interferants, e.g., mucins in saliva, so as to increase the sensitivity of the testing procedure. Once again, in this embodiment, a removable barrier such as strip 46 is provided which is removed in order to start the lateral flow immunoassay to proceed. This strip may be pulled out when desired to start the testing process following a suitable period of incubation, and it is further possible that the barrier might be constructed of a dissolvable material which is only designed to breakdown after the given incubation period has elapsed.

Figure 11B:
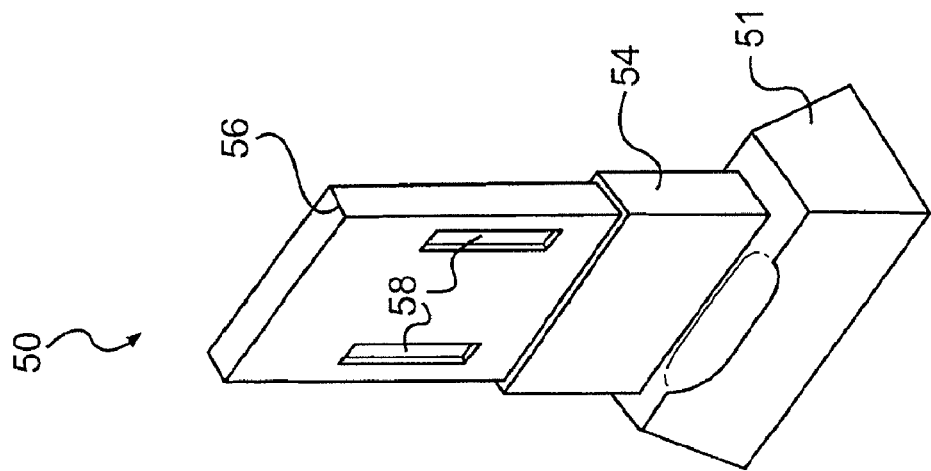
Figure 11A:
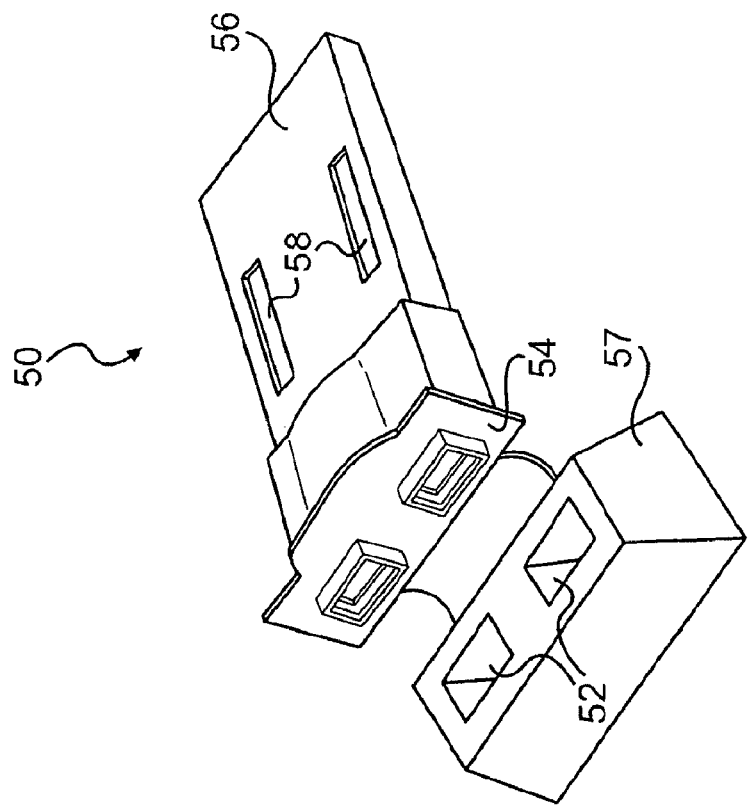
Figure 11C:
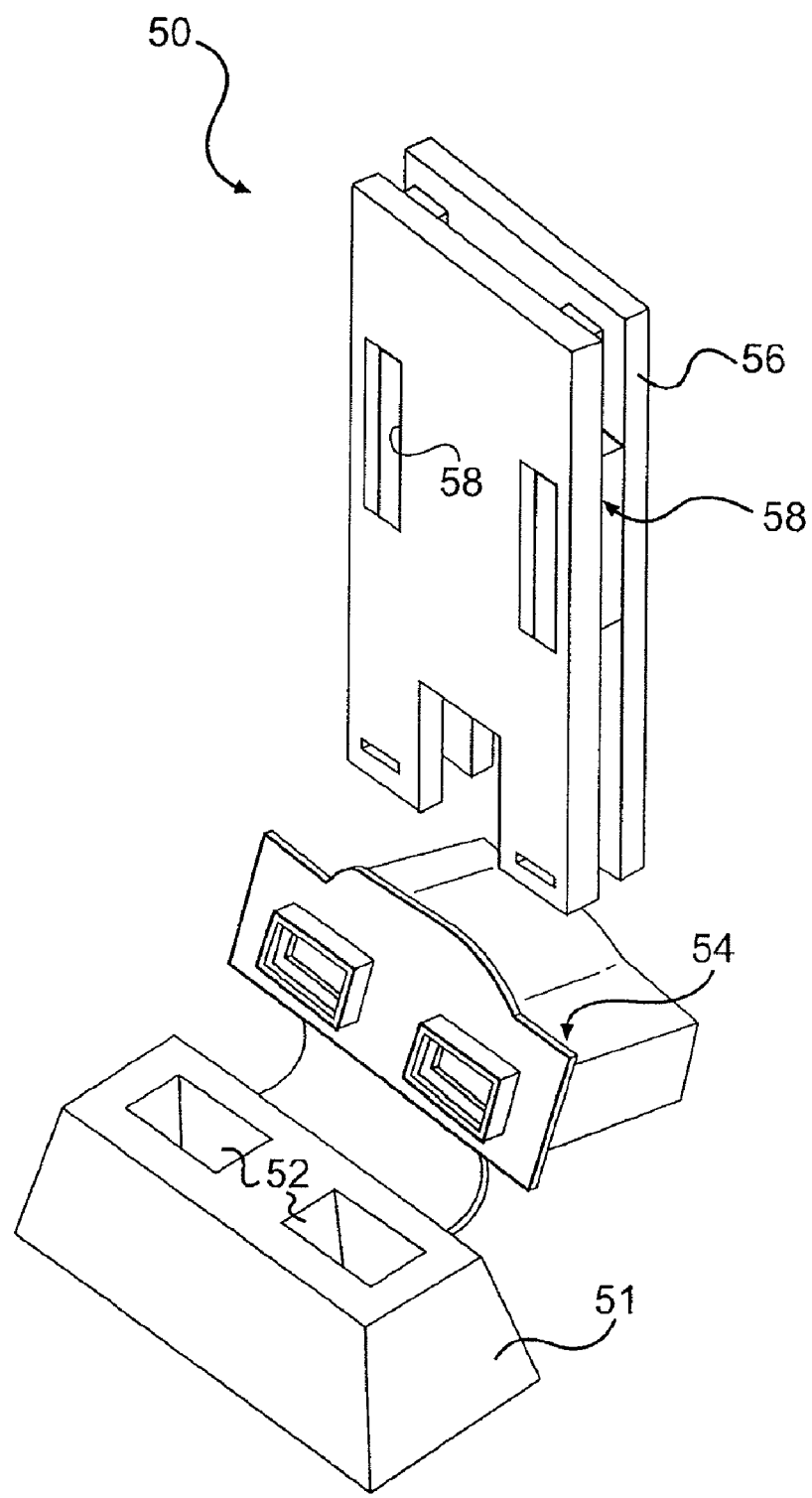

In yet a further alternative embodiment of the testing device of the present invention is shown in FIGS. 11a-11e which comprises a device which can be utilized in road-side drug testing when so desired. In the alternative testing device 50 of the present invention, which is generally shown in the perspective views of FIGS. 11a and 11b, the device comprises a lower half 51 which contains reaction wells 52 wherein an identifying reagent such as gold-labelled antibodies as described above may be stored. As indicated above, the gold labelled antibodies 55 may be placed at the bottom of the reaction wells 52 and will be utilized so as to allow drugs or other analytes targeted in a particular test to be detected in a lateral flow immunoassay. As indicated above, the reaction wells 52 will receive the sample included in the buffer solution which can be introduced by dropper or pipette means as also described above. Connected to the lower portion 51 is an upper base lid 54 which is best observed in the break-away drawing shown in FIG. 11c. The upper base lid 54 is designed to snap fit on top of the lower portion 51 so as to provide a seal for reaction wells 52 which will keep the sample and buffer in the reaction wells from spilling. In addition, the upper base lid 54 provides a base for a strip holding means such as cassette 56 which will hold the test strips 58 outside of the reaction wells until it is time to conduct the immunoassay. As can be observed in FIG. 11c and in the cut-away view of FIGS. 11d and 11e, the cassette 56 is designed so that when incubation of the sample and buffer solution with the colloidal gold antibody has been completed, the cassette 56 may be brought downward so that test strips 58 will be placed in contact with the solution in reaction wells 52 so as to allow the conducting of the lateral flow immunoassay test in accordance with the present invention. In FIG. 11*d*, the testing device 50 is shown with the test strips 58 in an outward position where they are not in contact with the solution in the reaction wells 52, and in FIG. 11*e*, the testing device is shown wherein the cassette has been pushed downward so that the test strips are placed in contact with the solution in the reaction wells 52 so as to initiate the immunological testing in accordance with the invention.

Still other testing devices and systems compatible for use with the collector wand and methods of the present invention include those devices as described in detail in other U.S. patent applications including U.S. Ser. No. 11/443,050, filed May 31, 2006, U.S. Ser. No. 11/252,599, filed Oct. 19, 2005, and U.S. Ser. No. 11/167,227 filed Jun. 28, 2005, all of said applications incorporated herein by reference.

Accordingly, it is contemplated that the test device of the present invention may included reaction wells that are capped so that the solution of sample and buffer may mix with the label such as colloidal gold particles without any danger of the solution spilling out of the reaction well, and this capping would also permit additional shaking as desired to even further impart energy to the solution and afford even greater breakdown of mucins and increase the sensitivity of the testing.

In summary, in the present invention, a general process for collecting and testing a body fluid sample such as saliva is provided wherein a latchable collector wand having an absorbent sponge at its distal end can absorb a body fluid such as by insertion into the mouth or nose of the person to be tested, and sponge is swabbed until it becomes fully saturated. The collector wand is then removed and the body fluid is extracted from the sponge end into a suitable container or vial which preferably contains a buffer agent or other reagent which can begin the process of breaking down the interferants in the sample such as mucins when the body fluid being tested is saliva. As set forth above, when the sponge end of the wand is placed in the buffer solution so that the buffer solution becomes absorbed in the sponge, the handle of the latchable collector wand of the invention is brought down over a stem having protrusions or ledges which will be caught and retained by the latch in the interior cavity of the handle, and in the locked position, the handle will compress the sponge so that a maximum amount of the body fluid is expressed from the sponge and into the buffer solution. This buffer container or vial is preferably sealed such as with a removable cap so that one may also impart energy to the container or vial such as by shaking in order to promote the mixing of the sample and the buffer. The resulting buffer solution is then dispensed using a dropper or pipette into a reaction well of the test device which includes a suitable identifying reagent to be used in conjunction with an immunoassay test strip. This identifying reagent may be a complex such as a gold-labeled antibody and may be in the form of a dry dot or a pellet, or other suitable form.

As indicated above, after a period of incubation of the sample solution with the identifying reagent, an immunoassay test strip which is designed to test for particular drugs of abuse or other analytes via a lateral flow immunoassay, and which is configured in conjunction with the labelled antibody so as to evidence the presence or absence of the target drug or analyte in the sample, is introduced into the reaction well to allow the lateral flow immunoassay to take place. The immunoassay may be carried out by either dropping the test strip into the reaction well by means of a slidable test strip holder, or by other means such as by the removal of a barrier between the reaction well and the test strip which allows the sample solution to come into contact with the test strip and start the immunoassay. In the preferred process, in addition to a visible means for determining the presence or absence of the drug or analyte being tested, the test strips will contain means to evidence that the test has been successfully conducted, i.e., the lateral flow process has been completed, so that the person reading the test results will know that the test is a valid one. The test result is preferably viewed at a specific portion of the strip, such as that portion which coincides with an opening in the testing device housing.

Thus it can be seen that the present invention discloses a body fluid testing device including a latchable wand which facilitates the expression of the bodily fluid from a collector sponge, and which allows for testing of drugs of abuse or other analytes from such fluids with high sensitivity.

It will be understood that the description of the embodiments provided herein are merely exemplary of the invention, and thus there other embodiments and modifications not described above which are contemplated as part of the present invention and which thus are considered to be within the scope of the invention.

What is claimed is:

1. A process for determining the presence or absence of a drug of abuse or other analyte in a body fluid sample taken from the subject to be tested comprising the steps of:
    (a) collecting a body fluid sample from the subject using a latchable extractor wand that contains a sponge for collecting the fluid specimen from the subject, a means for compressing the sponge so that the body fluid may be expressed, said means comprising a movable handle that can move downward along a stem so as to compress the sponge against a fixed surface at the end of said stem, and a means for latching the handle into a locked compression position over said stem when the sponge is compressed by the handle;
    (b) expressing the body fluid sample from the sponge to a vial containing a buffer solution by moving the handle into the locked compression position so as to compress the sponge and then imparting energy into the buffer solution so as to promote the breakdown of the sample and to reduce viscosity of the sample;
    (c) dispensing the solution of expressed body fluid and buffer from the vial to a reaction well containing a reagent capable of identifying a drugs of abuse or other analyte, and allowing a suitable incubation time to occur to allow the expressed body fluid and buffer to mix with the identifying reagent; and
    (d) allowing the solution in the reaction well to contact an immunoassay test strip so as to conduct a lateral flow immunoassay and determine the presence or absence of a drug of abuse or other analyte in the body fluid sample.

2. The process of claim 1 wherein the vial is sealed following the expression of the body fluid sample into the buffer solution.

3. The process of claim 1 wherein energy is imparted to the body fluid sample and buffer solution by means of shaking.

4. The process of claim 1 wherein energy is imparted to the body fluid sample and buffer solution by means of a chemical reaction.

5. The process of claim 1 wherein the identifying reagent is a gold-labeled antibody.

6. The process of claim 1 wherein the solution in the reaction well is allowed to contact the immunoassay test strip by means of a test strip holder which brings a test strip from a first position wherein said test strip is not in contact with the solution in the reaction well to a second position wherein said test strip is placed in contact with the solution in the reaction well.

7. The process of claim 1 wherein the solution in the reaction well is allowed to contact the immunoassay test strip by means of a removable barrier which separates the solution in the reaction well from the immunoassay test strip which can be removed so as to allow the solution in the reaction well to contact the immunoassay test strip.

8. The process of claim 7 wherein the removable barrier is made of a dissolvable material.

9. The process of claim 8 wherein the removable barrier is constructed to dissolve at a predetermined time to coincide with the completion of the incubation of the sample solution in the reaction well.

10. The process of claim 1 further comprising a step of imparting energy to the reaction well following introduction of the body fluid and buffer solution, but before the body fluid and buffer solution is contacted with the immunoassay test strip.

11. The process of claim 10 wherein said energy is imparted by shaking the reaction well.

12. The process of claim 10 wherein said energy is imparted by means of a chemical reaction.

13. The process of claim 1 wherein the reaction well are capped following introduction of the solution containing the body fluid and buffer.

14. The process of claim 1 wherein the body fluid that can be absorbed by said sponge is selected from the group consisting of saliva, blood, urine, cerebrospinal fluid, nasal fluid, buccal cavity fluid, swab, tears, sweat, vaginal secretions, ear wax, and other bodily fluids.

* * * * *